(12) United States Patent
Kraus

(10) Patent No.: US 8,932,356 B2
(45) Date of Patent: Jan. 13, 2015

(54) INTERVERTEBRAL IMPLANT

(75) Inventor: Kilian Kraus, Werneck (DE)

(73) Assignee: Henning Kloss, Ennetbürgen (CH)

( * ) Notice: Subject to any disclaimer, the term of this patent is extended or adjusted under 35 U.S.C. 154(b) by 1267 days.

(21) Appl. No.: 12/744,838

(22) PCT Filed: Nov. 27, 2008

(86) PCT No.: PCT/DE2008/001994
§ 371 (c)(1),
(2), (4) Date: Dec. 8, 2010

(87) PCT Pub. No.: WO2009/068021
PCT Pub. Date: Jun. 4, 2009

(65) Prior Publication Data
US 2011/0082551 A1 Apr. 7, 2011

(30) Foreign Application Priority Data

Nov. 27, 2007 (DE) .......................... 10 2007 056 993

(51) Int. Cl.
*A61F 2/44* (2006.01)
*A61F 2/30* (2006.01)
*A61B 17/68* (2006.01)
*A61F 2/36* (2006.01)
*A61B 17/15* (2006.01)
*A61F 2/38* (2006.01)
*A61F 2/28* (2006.01)
*A61B 17/80* (2006.01)

(52) U.S. Cl.
CPC ............ *A61F 2/30771* (2013.01); *A61B 17/68* (2013.01); *A61F 2/3601* (2013.01); *A61F 2/3603* (2013.01); *A61F 2/3662* (2013.01); *A61F 2/4465* (2013.01); *A61B 17/152* (2013.01); *A61F 2/38* (2013.01); *A61F 2002/2835* (2013.01); *A61F 2002/2892* (2013.01); *A61F 2002/30332* (2013.01); *A61F 2002/30622* (2013.01); *A61F 2002/30736* (2013.01); *A61F 2002/30785* (2013.01); *A61F 2002/3092* (2013.01); *A61F 2002/3654* (2013.01); *A61F 2220/0033* (2013.01); *A61F 2310/00017* (2013.01); *A61F 2310/00023* (2013.01); *A61F 2310/00029* (2013.01); *A61F 2310/00131* (2013.01); *A61B 17/8095* (2013.01)
USPC ....................................... 623/17.16

(58) Field of Classification Search
USPC ....................................... 623/17.16
See application file for complete search history.

(56) References Cited

U.S. PATENT DOCUMENTS

| 5,702,449 A | 12/1997 | McKay |
| 5,732,469 A | 3/1998 | Hamamoto et al. |
| 6,010,336 A | 1/2000 | Shimotoso et al. |
| 2005/0021151 A1 | 1/2005 | Landis |
| 2005/0112397 A1 | 5/2005 | Rolfe et al. |
| 2006/0141012 A1 | 6/2006 | Gingras |

FOREIGN PATENT DOCUMENTS

| DE | 19610715 | 6/1997 |
| EP | 1772108 | 4/2007 |
| JP | 56-80121 | 11/1979 |
| WO | 9640015 | 12/1996 |

*Primary Examiner* — Sameh Boles
(74) *Attorney, Agent, or Firm* — Meyertons, Hood, Kivlin, Kowert & Goetzel, P.C.; Eric B. Meyertons

(57) ABSTRACT

Embodiments are directed to bone-joining or bone-bridging intervertebral implants with an inner channel-type structure of channels, which extend parallel from a bone contacting-surface of the implant to the inside of the implant, whereby the channels are connected by lateral openings.

33 Claims, 11 Drawing Sheets

Tibia

INTERVERTEBRAL IMPLANT

BACKGROUND OF THE INVENTION

1. Field of the Invention

The present invention is direct to intervertebral implants, so-called cages, with an inner channel-type structure.

2. Description of the Relevant Art

In the prior art solid and hollow implants are known in particular in the area of the spine, which either prevent the ingrowth of bone cells due to their solid structure or have a cavity which is too large to be completely filled with endogenous bone cells within a reasonable time and therefore are usually filled artificially with a bone substitute material or bone chips.

The aim of a fusion is the formation of bones, for instance by cages in the spine area, to achieve a as long as possible a stability. The growth of the bones through the implant is insofar advantageous that the bone cells can renew themselves, like elsewhere in the body and thus guarantee a long-term stability. The cages thus serve as a temporary placeholder so that the intervertebral disc space does not sink in, and thus loses height. Therefore, the cages primarily have to take over static functions, at least until the formation of bones through the implant has taken place. A quick and stable growth of bones through an artificial intervertebral implant, such as a cage, is principally desired, because such implants come closest to the natural intervertebral disc and represent the most advantageous embodiment for the patient.

The disadvantage of a solid implant such as a solid cage is obviously that a growth of bones through the implant is not possible, i.e. the implant must permanently take on the supportive function and thus is less effective in the long-term. If an implant is used as a pure spacer, there is further the risk that the implant sinks into the bone and the desired distance is no longer guaranteed. Such drawbacks could be avoided for example, that the bones grow through the implant naturally.

Hollow implants, such as hollow cages are used with or without bone replacement material. These implants, however, have the disadvantage that the bones would have to fill a large cavity, if no bone replacement material is used to fill the implants and therefore the implant would have to take on the supportive function for too long with the above-described disadvantages. If bone replacement materials are used, they serve to stimulate the growth of bones. Since blood is the catalyst for the formation of bone but the inner cavity of the cage is filled with bone replacement material and is therefore not sufficiently supplied with blood, a natural growth of bones through the partly with bone replacement material filled cage is insufficient. This in turn means that a growth of bones through a cage partly filled with bone replacement material does also not take place in the desired manner.

Therefore, it would be ideal to have a bioresorbable artificial intervertebral disc, which takes over the support function as long as the endogenous bones have replaced it and can take over the support functions. Such embodiments have not been realized previously due to a lack of suitable materials. One reason for this is the fact that no biodegradable materials are available, which ensure sufficient stability while the bone is building up, and the rate of degradation can also not be regulated sufficiently accurate, because the formation of the bone and the resorption of the implant must occur exactly at the same speed so that no transition structure is formed, which could collapse.

However, bone-joining or bone-bridging implants would be desirable, which on the one hand provide a sufficient mechanical stability and on the other hand can be grown through as completely as possible with endogenous bones.

SUMMARY OF THE INVENTION

In one embodiment, intervertebral implants are provided that promote the ingrowth of endogenous bones best possible, thereby supporting optimal endogenous bone development and guarantee sufficient stability until the formation of endogenous bones.

In one embodiment, an intervertebral implant has two surfaces for contacting two vertebral bodies, an outer sheath and an inner structure and wherein the inner structure is fixated by a plurality of channels and the channels each have a cross-sectional area of 8,000 µm2 to 7,000,000 µm2 and the channels extend parallel to one another along the longitudinal axis of the spinal column and the channels are connected by openings to each other.

BRIEF DESCRIPTION OF THE DRAWINGS

Advantages of the present invention will become apparent to those skilled in the art with the benefit of the following detailed description of embodiments and upon reference to the accompanying drawings in which.

DETAILED DESCRIPTION OF THE PREFERRED EMBODIMENTS

Figure 1:
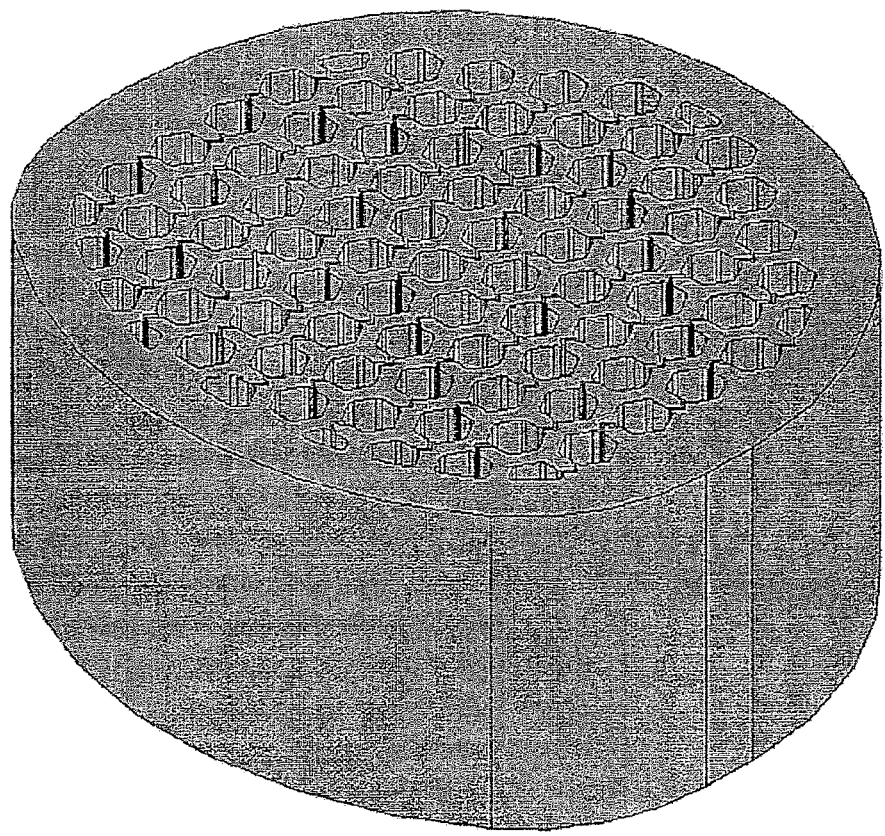
FIG. 1 shows a perspective view of an bone joining intervertebral disc implant, such as a cage. The implant is shown exemplary with an oval shape, which however is not mandatory. The outer wall of the implant is solid and the implant consists of a physiologically acceptable material, especially a metal or metal alloy. In the inner area of the implant the honeycomb structure of continuous channels can be seen, which are connected with each other through openings.

Embodiments herein relate to metallic bone joining or bone-bridging intervertebral implants in the form of artificial discs, wherein the artificial disc implant exhibits at least one bone-contacting surface and an inner structure consisting of a plurality of channels with defined cross-sectional areas or radii and the channels are connected via openings with each other, so that a three-dimensional network of canals is formed.

It was surprisingly found that bone-joining or bone-bridging intervertebral disc implants particularly well grow together with the contacted bone, when the surface of the implant is not smooth or not rough or not porous, but has a channel structure, wherein the channels are connected to each other through openings and have a defined structure. The nature and the symmetry of the channel structure is described in detail below.

The term "bone joining" or "bone-bridging" is to be understood, that the implant is directly in contact with a bone that means at least a part of the surface of the intervertebral disc implant touches a bone.

As examples of such intervertebral disc implants or intervertebral implants should be mentioned in particular cages for cervical, thoracic or lumbar application (such as, for example, ALIF-cages, PLIF-cages and TLIF-cages). Intervertebral implants are also called interbody vertebral elements, or implants for intersomatic fusion, or implants for intercorporeal vertebral interbody fusion.

The aforementioned implants usually include completely of a hard material, especially a metal or metal alloy such as titanium, zirconium, oxidized zirconium, hafnium, platinum, rhodium, niobium, surgical stainless steel, CoCr-steel (cobalt-chromium), tantalum but can also be made of fiber reinforced plastics (glass-/carbon-fibers with a corresponding matrix), PEEK [poly(ether etherketone)], or polymer materials in general. Moreover, metals such as aluminum, medical steel, and/or gold can be added to the metal alloys.

One-piece disc implants such as intervertebral implants, usually exhibit a solid sheath without a channel structure in order to ensure sufficient stability of the implant. The term "solid" as used herein means that the outer sheath has no openings, i.e. no openings of channels of the inventive channel structure or openings of connecting channels between the channels of the inventive channel structure right up to such a number of openings of channels or connecting channels of the inventive channel structure that the outer sheath is not deformed at the 5-fold, preferably at the 8-fold, particularly preferably at 10-fold the pressure exerted by the spine in the direction of the longitudinal axis of the spinal column, i.e. the openings are not compressed.

In an embodiment, the channel structure inside of the cage or the artificial disc implant is used for direct stimulation of bone growth and less for the stabilization of the entire implant. The mechanical stability of the intervertebral implant, the cage, is conferred by an outer sheath, which is designed for one, to withstand the high pressures of the spine and to prevent the sinking of the implant into the vertebral bone, so that the distance between two vertebral bodies, defined by the height of the outer sheath, can be maintained. So the outer sheath is solid, i.e. the portion of the intervertebral disc implant, which surrounds the inner channel structure, and is not a part of the inner channel structure. The term "solid" should be understood that this outer sheath is preferably not traversed by channels, it contains no holes and none of the channels nm through the outer sheath and end on its outer surface. Thus, preferably no blood flow can take place through the outer sheath. The outer sheath loses its supportive function gradually the more the inner channel structure is grown through with bones.

The outer sheath can also be referred to as cortical outer wall of the intervertebral implant. The intervertebral implants used for intersomatic fusion, should ideally correspond to the base area of the adjacent vertebral bodies.

The available space for the growth of bones should be maximized but still allow a quick growth of endogenous bone cells through the implant. Additionally, in the first moment of medical care, i.e. after implantation, the implant has to take over static functions and it must be prevented that the implant offers too little support surface area for the vertebral body and it therefore sinks into the vertebral body under the influence of load.

The particular load-bearing structure of the vertebral body is the circular peripheral corticalis. Ideally, the solid wall of the cage rests between the circular running cortical walls of the adjacent vertebral bodies, so that the corticalis has a support base available, which prevents the sinking of the cages into the vertebral body.

In the area of spongiosa, i.e. the well-vascularized bone centrally located in the vertebral body, lies the honeycomb structure of the cage to ensure a perfect growth of bones.

The implants can be manufactured by standard techniques, for example, using laser technology and laser cutting procedures, laser fusion, e.g. Lasercusing and therefore can assume any shape.

The cages are thus preferably one-piece, including completely or at least to 90 wt-% of metal or a metal alloy, are not porous, such as ceramics can be, but have a defined inner channel structure, which supports the blood flow and thus creates the best possible conditions for endogenous bone growth and have an outer shell, which is responsible for the stability at least as long as the newly formed bone cannot take over this function.

The term "one-piece intervertebral disc implants" or "one-piece cages" refers only to the implant itself and not to any fasteners. Such disc implants for example, can be screwed into the adjacent vertebral bodies. The used fasteners, for example screws are not taken into account when using the term "one-piece" and are referred to as accessories to the disc implant as well as the implantation tool. In addition, natural materials such as natural bone material are not components of the intervertebral disc implant and no artificial bone material has to be used or is used for the implantation. The cages are thus in accordance with this definition preferably in one-piece. Two-piece embodiments are also possible, wherein the implants are made up of maximal three pieces, preferably of not more than two pieces, whereby the other parts generally relate to intended attachment means for the cage such as removable panels for mounting screws or hooks or fastening nails or the like, which usually can be made optional to the implants.

The implants are not assembled by a modular system or from several individual components or parts, which eventually can be difficult to combine, or could be free to move in a translational, rotational or sliding adjusting manner against each other, and have an outer sheath with a defined shape that does not change its form and dimension after the implantation.

One possibility is, however, to manufacture the inner honeycomb structure or channel structure separately from the outer sheath and to assembly them after separate production, so that ultimately there is again a one-piece implant. As described above, the outer sheath is solid, i.e. only so many cutouts, holes or openings may be contained therein, that no deformation takes place due to the pressure of the spinal column until the complete growth of endogenous bone through the implant. It is preferred that the solid outer sheath exhibits no gaps, holes or openings.

The channel structure starts at the bone-contacting surface of the implant, so that the openings of the channels are facing the bone, i.e. the upper openings are facing the upper contacted vertebral body and the lower openings of the channels to the lower vertebral body.

In bone joining or bone-bridging implants of the spine area as well as with the implants, the contact surfaces of the implants are generally flat to the respective bone and the channels extend along the longitudinal axis of the spine away from the bone contact surface.

The contact surface of the cage is understood to be the surface, which comes into contact with the overlying vertebral body and the opposite surface of the cage, which comes into contact with the underlying vertebral body.

But the contact surface with the bone has not to be designed flat, as is the case with the intervertebral implants of the prior art, but can also have an asymmetrical form. It is certainly more preferable, when the inner channel structure extends slightly over the outer sheath in the direction of the overlying vertebral body as well as in the direction of the underlying vertebral body as will be described below in more detail. The part of the inner channel structure extending over the outer sheath sinks or presses in the overlying or underlying vertebral body respectively and thus leads to an intended injury of the surface of these two vertebral bodies, whereby the growth of bones and the blood flow is further increased.

Thus, the channels start at the bone-contacting surface of the implant, whereby the inner channel structure exhibits a flat surface to the overlying vertebral body and a flat surface to the underlying vertebral body. Preferred, however, is a convex curve, i.e. to the vertebral body directed curve of the surface of the inner channel structure, whereby the contacting surface to the overlying vertebral body can be designed convex and/or the underlying vertebral body contacting opposite surface of the inner channel structure can be designed convex. The convex curvature of the inner channel structure has a height measured at the highest point of the curvature of 0.1 mm to 5 mm.

Individual channels, or at least 75% of all channels, preferably at least 85% of all channels and particularly preferably at least 95% of all channels have a cross-sectional area of 8,000 $\mu m^2$ to 7,000,000 $\mu m^2$, preferably from 50,000 $\mu m^2$ to 3,100,000 $\mu m^2$, more preferably in the range of 100,000 to 800,000 $\mu m^2$, even more preferably in the range of 125,000 to 650,000 $\mu m^2$ and especially preferably in the range of 160,000 to 570,000 $\mu m^2$.

The expression that 85% of all channels have a cross-sectional area within the aforementioned areas means that out of 100 channels, 85 channels have a cross-sectional area in the aforementioned ranges and the remaining 15 channels can have a smaller or larger, as well as a significantly smaller or significantly larger cross-sectional area.

The channels can have any desired shape and be designed round, oval, triangular, square, pentagonal, hexagonal, heptagonal, octagonal or polygonal as desired. Preferred, however, are embodiments with internal angles greater than 90°, beginning with a pentagon over a polygon to a circle or an oval. Also preferred are pentagonal, hexagonal, heptagonal and octagonal embodiments and, in particular hexagonal channels.

For round channels, the cross-sectional area is equal to the circular area and can easily be calculated in accordance to $\pi r^2$, where r is the radius of the channel.

In terms of round or approximately round channel forms it is preferred if the channels or at least 75% of all channels, preferably at least 85% of all channels and particularly preferably at least 95% of all channels exhibit a diameter of 100-3,000 µm, preferably 250-2,000 µm, more preferably 350-1,000 µm, even more preferably 400-900 µm, and most preferably 450-850 µm.

In polygonal channel shapes the diameter is referred to as the distance between two opposite parallel surfaces in even-numbered polygons (square, hexagonal, octagonal, etc.) or the distance of a corner point to the center of the opposite surface in odd-numbered polygons (triangle, pentagon, heptagon etc,).

The thickness of the channel walls is 20 µm to 700 µm, preferably 30 µm to 550 µm, and more preferably 40 µm to 400 µm. The diameter of the channels is preferably from 2-times to 4-times the thickness of the channel walls (channel wall thickness). The outer sheath has a thickness of 500 µm to 1,500 µm, preferably from 700 µm to 1,300 µm and most preferably from 850 µm to 1,100 µm. The thickness of the outer sheath preferably corresponds to one-time to 2-times the diameter of the channels. The thickness of the cuts or connecting channels or the diameter of the openings is preferably one-third to one-tenth of the thickness of the channels.

Channels with the aforementioned diameter or the aforementioned cross-sectional area extend from the surface of the implant, which is attached at the bone, in the inside of the implant. The channels of the preferred one-piece implants with opposite bone-contacting surfaces such as the cages, extend preferably through the implant to the opposite bone-contacting surface.

The channels of the implants do preferably not end at the height of the outer sheath, but reach to a maximum of 10 mm beyond its height.

The design of the channels follows a symmetry. It should be noted that a randomly originated channel network, such as exists for example in porous structures or sponges without symmetry are not satisfactory. The same is true for channels, which erratically change their directions and diameters or which are in a sequence and/or form created randomly and/or arbitrarily by multi-layer systems. In such systems the blood flow is only increased in some areas and bone cell formation can only be seen in certain areas or punctual, so that a growth through the entire implant with bone cells is slowed down or takes only place in part.

According to an embodiment, the channels run substantially parallel to each other and are straight, i.e. the channels have no turnings, bends, curves or the like, but run from their opening on an outer surface of the implant substantially parallel into the implant or a portion of the implant and end in the inside of the implant, or preferably nm through the implant up to the opposite outer surface of the implant. Moreover, the channels preferably do not change their radius or diameter, neither continuously, nor abrupt or gradual, regardless of whether they are round, oval or polygonal channels.

The term "substantially parallel" is to be understood that there are certain manufacturing tolerances, and apart from these tolerances, the channels rim parallel to each other.

Furthermore, the diameter of the channels do not change during their course, i.e. also, apart from manufacturing tolerances, the channels have substantially the same diameter from their beginning to their end.

It is also not mandatory that all channels start on the bone-contacting surface, i.e. to be in direct contact with the bone. Up to 30% preferably up to 20% of all channels can also begin in one area of the implant that is not directly in contact with the bone, i.e. preferably these channels start laterally of the bone-contacting surface.

On the other hand it is not necessary that the channels also end at a bone-contacting surface, which would only be the case anyway with one-piece bone-joining or bone-bridging implants. Up to 100% of all channels can also end at a surface not contacting the bone, but it is also possible that up to 100% of the channels end on the opposite bone-contacting surface, which is preferred for manufacturing reasons for one-piece cages according to an embodiment.

Moreover, it is preferred that, apart from the solid outer sheath of the implant, per $cm^2$ bone-contacting surface at least 50 channels start, preferably at least 100 channels and more preferably at least 150 channels. The channel structure comprises 20-1,000 channels per $cm^2$, preferably 50-750, more preferably 100-500, still more preferably 125-350 and especially preferably between 150 and 250 channels per $cm^2$.

Furthermore, the channels are interconnected. The channels are connected through openings with each other, wherein each channel has at least one opening to an adjacent channel. It is also preferred that the outer channels, i.e. those channels which form the outer row of the entire channel-type structure and abut to the solid outer sheath, have at least one opening to an adjacent channel and the channels which lie inside the channel-type structure have at least one opening to two adjacent channels, i.e. comprise absolutely at least two openings.

Moreover, it is preferred if the openings are arranged in a way that all channels are connected with each other, i.e. the entire channel-type structure could theoretically be filled through one opening of one channel with liquid such as blood. So preferably a three-dimensional interconnectivity of the entire structure is created.

The openings or so called connecting channels, can be designed as desired and exhibit the form of holes or cuts, round, circular, point-shaped, punctiform, cylindrical, oval, square, wedge-shaped or any other configuration.

It is also preferred that the openings between the channels follow a pattern, i.e. a symmetry or a recurring order. It is therefore preferred that the openings between the channels run either along the longitudinal axis of the channels and the openings can have a maximum length, which corresponds to the length of the interconnected channels. This type of openings, which run along the longitudinal axis of the channels, are preferably cuts, preferably wedge-shaped cuts in the channel walls or channel claddings.

Figure 2:
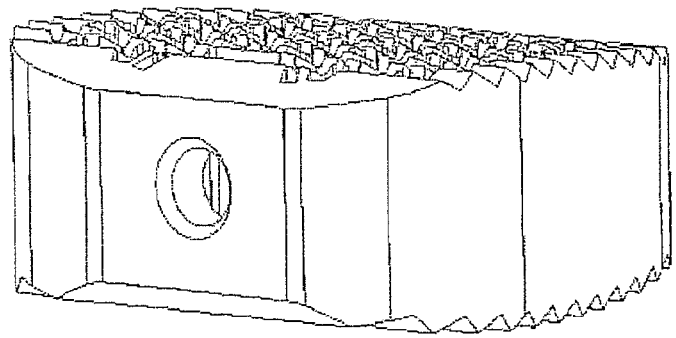
FIG. 2 shows the intervertebral implant from a side view.

Another type of openings is preferably designed round or oval and runs vertical to the longitudinal axis of the channels. The longitudinal axis of the channels run along the longitudinal axis of the spine. These openings are cut into the implant with e.g. a laser and run through the outer wall of the implant in the direction of the opposite surface, thereby linking the channels on this line with each other. To ensure the above-described stability, the openings or connecting channels may also end in the inside of the cages without penetrating the opposite outer sheath. It is therefore preferred that these connecting channels pass through the outer sheath and end in front of the inner surface of the opposite outer sheath. However, preferred are openings or incisions, which run along the central axis of the channels and cut the wall of a channel along its entire length as a cut or tapered cut. These longitudinal cuts along the channel wall are naturally arranged in a way that several cuts in adjacent channel walls do not cut out sections of channel walls of the whole structure. Taking a look at FIG. 2 with the hexagonal channels and the wedge-shaped connecting channels or incisions, one could divide the channel walls in lateral wall areas and anterior-posterior wall areas. In FIG. 2, for example, only the lateral wall regions are cut in, so that all channel walls are at least connected in two places with the solid outer sheath and none of the wall segments, not even a segment of several channel wall areas of several channels of the total channel structure has been cut out or detached.

The diameter or the thickness of the openings is in the range of 0.1 µm to 1,000 µm, preferably in the range of 1 µm to 500 µm, more preferably 10 µm to 200 µm, even more preferably in the range of 30 µm to 100 µm and most preferably in the range of 50-80 µm.

Furthermore, the openings can extend along the longitudinal axis of the channels, this is referred to as continuous, and can even am from one bone-contacting surface to the opposite bone-contacting surface and thus have the length of the channels themselves.

The openings may also occur in the form of drill-holes vertical to the longitudinal axis of the channels through the implant or as after certain intervals recurring openings in the channel walls connecting the channels with each other.

The design of the channels themselves is not essential, but their presence. It is obvious to a skilled person, that too many openings can affect the stability of the implant, so that a skilled person knows how to determine the number, size and location of the openings depending on the type of the implant.

Furthermore, the diameter or the thickness of the openings should be smaller than the diameter or the thickness of the channels and preferably less than one-tenth of the thickness of the channels.

Principally, the holes can be described as vertically to the longitudinal axis of the channels extending connecting channels. The channel structure consists preferably of substantially parallel channels, which also preferably extend parallel to the connecting channels.

It also goes without saying that not the whole implant must display the channel structure, but only the areas of an implant, which come into contact with the bone or particularly are embedded in the bone. However, it is still preferred if the inner channel structure of the intervertebral implants or cages extends from the underside of the overlying vertebral body to the upside of the underlying vertebral body. The interior of the implant is defined by the outer sheath.

Figure 3:
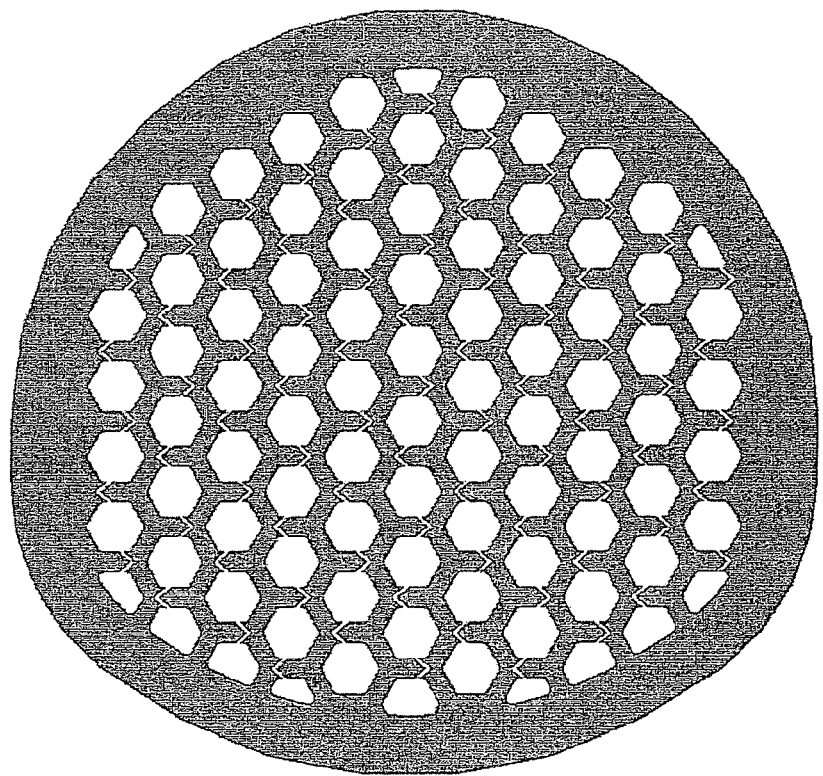
FIG. 3 shows a view of the implant along the longitudinal axis of the channels. The side walls of the channels are visible as honeycomb pattern and the openings between the channels are visible as a wedge-shaped incisions. In addition, it can be seen that the channels are continuous, i.e. pass from the top of the implant to the bottom.
Figure 4:
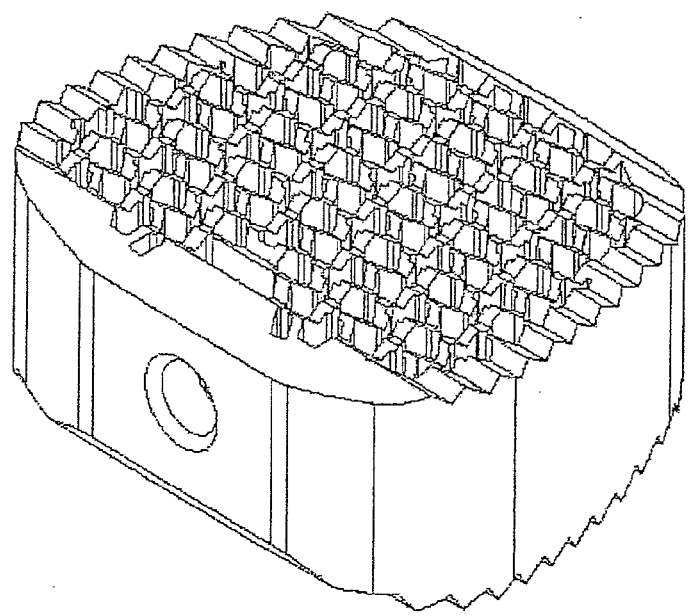
FIG. 4 shows an intervertebral implant from a perspective view. The well serrated top and serrated bottom of the implant can be seen, which contribute to the stabilization of the position of the implant.

In the embodiments of cages, substantially parallel continuous channels in particular have been proved to be advantageous, which are connected by wedge-shaped longitudinal incisions along the longitudinal axis of the channels, as shown in FIGS. 2, 3 and 4.

Furthermore, implants are preferred where the honeycomb structure, i.e. the inner channel structure, rises slightly over the substantially flat bone-contacting surface. Especially, if the honeycomb structure of the implant protrudes over a solid border, the advantage of a high surface friction and therefore a very good anchorage is given and at the same time, due to the low thickness of the honeycomb walls, the possibility of mechanical movement of the same arises, which promotes the growth stimulation of the bone.

The walls between the individual channels, i.e. the honeycomb walls or channel walls have a thickness of 1 µm to 3,000 µm, preferably 5 µm to 1,000 µm, more preferably 10 µm to 500 µm and particularly preferably from 50 µm to 250 µm.

Moreover, it is preferred that the openings in the inner channel structure are arranged in such a way that the entire structure permits micro-movements preferably friction-movements. Such movements are possible e.g. with a structure as shown in FIG. 2, wherein the single channels are connected by wedge-shaped longitudinal cuts in the lateral wall areas along the longitudinal axis of the channels. Thus, the individual channel walls can be shifted against each other according to the thickness of the wedge-shaped openings, so that micro-movements are possible.

If this type of configuration with the openings between the channels is combined with the configuration, where the inner channel-type structure rises like an island up to several millimeters over the basically flat bone-contacting area, i.e. is designed convex in the direction of the contacted vertebral body, this up to 10 mm raised portion of the honeycomb structure stimulates the growth of bone particularly well, because this elevated part digs slightly into the bone and through its property to permit micro-movements, it can follow the bone movements and also promotes the growth of bones through a slight but continuous stimulation.

Implants with bone growth stimulating surfaces are still a subject of research, without having achieved a satisfactory result yet. The previously described raised honeycomb structure with the ability to permit micro-movements, in particular microfriction-movements seems to be the long sought solution to stimulate bone growth in an optimal way and to lead to a rapid growth of bone through the entire implant.

This channel structure for bone-contacting, bone-joining or bone-bridging implants has surprisingly shown to be very advantageous in terms of an ingrowth of bone tissue and providing a solid adhering with the contacted bone.

Furthermore, the honeycomb structure combines the features of good mechanical stability and at the same time preserves optimal filling volume, so that a rapid and stable growth of bones through implant can take place.

Bone tissue generally comprises three cell types, osteoblasts, osteocytes and osteoclasts, whereby the developed bone also has a bone top layer of bone lining cells. The presence of blood is needed for optimal bone formation. In the formation of bones the osteoblasts, osteocytes and osteoclasts work together. Osteoblasts are bone producing cells and responsible for building and maintaining the bone. None active osteoblasts on the bone surface are called bone lining cells. Osteocytes are former osteoblasts that are incorporated in the bone tissue by ossification. They provide for the preservation of the bone by adjusting the bone resorption to the bone formation. Osteoclasts are responsible for the degradation of the bone. Through them, the thickness of the bone is determined and calcium and phosphate can be released from the bone. The osteoblasts are the cells responsible for bone formation. They develop from undifferentiated mesenchymal cells, embryonic connective tissue cells. They attach themselves to bones like dermal layers and indirectly form the basis for new bone substance, the bone matrix, especially by excreting calcium phosphate and calcium carbonate in the interstitial space. In this process they change to a scaffold of osteocytes no longer capable of dividing, which is slowly mineralized and filled with calcium.

The channel structure seems to promote the inflow of blood and thus osteoblasts, which fill the channel space quickly and lead to a significantly better growth of the bone together with the implant compared to what conventional implants are capable of.

Furthermore, the designed implants have the advantage compared to, for example, porous structures and sponges that they are not very deformable and are dimensionally stable, possess a defined shape and surface and can be handled by conventional implantation tools and can be implanted without running the risk to damage or destroy the implant or the channel-like structure in the implant.

In order to promote the adhesion of bone cells even more, the inner surfaces of the channels can be structured by, for example, any mechanical, chemical or physical roughening.

To suppress the growth of bacteria or other germs on the implant surface, it can be provided with antibiotics and the outer surface of the outer sheath for example can be provided with a drug eluting coating, in which agents such as antibiotics are stored and can be released continuously.

Bone-contacting Implants

Embodiments also relate to in bone implantable, bone-joining or bone-bridging implants with an inner channel-type structure.

A growth of bones through the implant is desired principally in any kind of bone joining or bone-bridging implants, in that the entire implant, such as bone screws or corrective wedges is grown through or in that mainly the area of anchorage of an implant, such as the anchor pin of a joint implant or artificial discs.

The disadvantage of a solid implant, such as for example a solid correcting wedge is obviously that no growth of bones through the implant is possible, i.e. the implant must permanently assume the support function and the anchoring of the implant takes only place at its outer surface, without any growth of bone into the implant which would lead to a much better hold. Thus, embodiments are directed in particular to at least partly insertable or implantable bone implants, which in the area that is inserted or implanted into the bone, exhibit the channel-type or honeycomb-type structure. If an implant is used as a pure spacer, there is the further risk that the implant sinks into the bone and the desired distance is no longer guaranteed. Such drawbacks for example could be avoided, if the bones grow through the implant naturally. In addition to that, the channel-type or honeycomb-type structure makes the use of bone substitutes or analogous bone chips or bone material accumulating during the implantation unnecessary.

Thus, preferred are in a bone applicable bone joining or bone-bridging implants, which provide a sufficient mechanical stability and can also be grown through as complete as possible with endogenous bones.

Such implants are described in FIGS. 11 to 19.

Embodiments relate to in the bone applicable bone-joining or bone-bridging implants, whereby the implants have at least one bone-contacting surface and an inner structure of a plurality of channels with defined cross-sectional areas or radii and the channels are connected via openings to each other, so that a three-dimensional network of channels with defined radii arises which also permits micro-movements.

It was surprisingly found that in bone applicable, bone joining or bone-bridging implants particularly well grow together with the contacted bone, when the surface of the implant is not smooth or not rough or not porous, but has a channel structure, wherein the channels are connected to each other through openings and have a defined structure. The nature and the symmetry of the channel structure is described later in detail.

The term "bone-contacting" or "bone-joining" or "bone-bridging" is meant to be understood that the implant is directly in connection with a bone, that means at least a part of the surface of the implant comes into contact with a bone.

As examples of such implants can be mentioned: spine implants, hip joint implants, shoulder joint implants, finger joint implants, ankle implants, toe joint implant, knee joint implants, ankle implants, wrist implants or general joint implants, implants for fusion of bone, radius head implants, endoprosthesis, anchoring pins of implants or for implants, dental implants, implants for the skull, corrective wedges, angle implants, implants for angulation (tibia), metatarsal surgery, connect rear foot surgery or generally implants, which connect bones or are implemented at least in part into a bone. Principally, any implant, which is used with a part in a bone, can be equipped with the channel-type or honeycomb-type structure.

The implants can be manufactured by standard techniques, for example, using laser technology and laser cutting procedures, laser fusion, e.g. lasercusing and therefore can assume any shape.

In the hip joint implants in particular the shaft of the hip implant is designed. In the knee joint implants, the femoral component and the tibial component and in particular their anchoring pins can be fitted with the channel structure. In particular, anchoring pins to be used in a bone are provided with the structure. As spinal implants in particular cages for the cervical, thoracic, lumbar application (e.g., ALIF cages, PLIF TLIF cages and cages) and artificial discs are to be named.

The aforementioned implants are usually made of a hard material, especially a metal or metal alloy such as titanium, surgical stainless steel, CoCr steel, tantalum, and can also be fiber-reinforced plastics (glass/carbon fibers with a corresponding matrix), PEEK [poly(etheretherketone)] or polymer materials in general.

For this reason, the channel structure is not in the region of articulating surfaces in multi-piece implants, e.g. intervertebral implants, e.g. artificial discs or knee joint implants.

One-piece implants such as cages usually have a solid sheath without a channel structure in order to ensure sufficient stability of the implant.

The term "articulating surface" in multi-piece implants is to be understood as the surface of an implant part, which may come in contact to the surface of the other part of the implant. As a contact surface on the other hand is understood the area, where in a particular state or moment, the surfaces of the two parts of the implant actually come into contact.

The channel structure starts at the bone-contacting surface of the implant, so that the openings of the channels face the bone.

In bone-joining or bone-bridging implants of the spine area, the contact surfaces of the implants with the respective bone are flat and the channels extend along the longitudinal axis of the spine away from the bone contact area.

The contact surface with the bone, however, has not to be designed flat, but can also have an asymmetrical shape, such as the stem of a hip stem, the femoral component of a knee implant, or can be round, as the stem of a tibial component of a knee implant, the acetabulum of a hip implant or angle implants, which are used in readjustment osteotomies. Furthermore, the contact surface with the bone can be jagged, serrated, convex or be provided with barbs to provide immediately after the implantation a better grip in addition to the following growth of bones through the implant.

Thus, the channels begin at the bone-contacting surface of the implant. Individual channels, or at least 75% of all channels, preferably at least 85% of all channels and particularly preferably at least 95% of all channels have a cross-sectional area of 8,000 $\mu m^2$ to 7,000,000 $\mu m^2$, preferably from 50,000 $\mu m^2$ to 3,100,000 $\mu m^2$, more preferably in the range of 100,000 to 800,000 $\mu m^2$, even more preferably in the range of 125,000 to 650,000 $\mu m^2$ and especially preferably in the range of 160,000 to 570,000 $\mu m^2$.

The expression that 85% of all channels have a cross-sectional area within the aforementioned areas means that out of 100 channels, 85 channels have a cross-sectional area in the aforementioned ranges and the remaining 15 channels can have a smaller or larger, as well as a significantly smaller or significantly larger cross-sectional area.

The channels can have any desired shape and be designed round, oval, triangular, square, pentagonal, hexagonal, heptagonal, octagonal or polygonal as desired. Preferred, however, are embodiments with internal angles greater than 90°, beginning with a pentagon over a polygon to a circle or an oval. Also preferred are pentagonal, hexagonal, heptagonal and octagonal embodiments and, in particular hexagonal channels.

For round channels, the cross-sectional area is equal to the circular area and can easily be calculated in accordance to $\pi r^2$, where r is the radius of the channel.

In terms of round or approximately round channel forms it is preferred if the channels or at least 75% of all channels, preferably at least 85% of all channels and particularly preferably at least 95% of all channels exhibit a diameter of 100-3,000 µm, preferably 250-2,000 µm, more preferably 350-1,000 µm, even more preferably 400-900 µm, and most preferably 450-850 µm.

In polygonal channel shapes the diameter is referred to as the distance between two opposite parallel surfaces in even-numbered polygons (square, hexagonal, octagonal, etc.) or the distance of a corner point to the center of the opposite surface in odd-numbered polygons (triangle, pentagon, heptagon etc.).

The thickness of the channel walls is 20 µm to 700 µm, preferably 30 µm to 550 µm, and more preferably 40 µm to 400 µm. The diameter of the channels is preferably from 2-times to 4-times the thickness of the channel walls (channel wall thickness). The outer sheath has a thickness of 500 µm to 1,500 µm, preferably from 700 µm to 1,300 µm and most preferably from 850 µm to 1,100 µm. The thickness of the outer sheath preferably corresponds to one-time to 2-times the diameter of the channels. The thickness of the cuts or connecting channels or the diameter of the openings is preferably one-third to one-tenth of the thickness of the channels.

Channels with the aforementioned diameter or the aforementioned cross-sectional area extend from the surface of the implant, which is attached at the bone, in the inside of the implant. The channels of the preferred one-piece implants with opposite bone-contacting surfaces such as cages or bone wedges, extend preferably through the implant to the opposite bone-contacting surface.

In implants with articulating surfaces the channels end preferably not on an articulating surface, but only reach through the implant completely, where the openings of the channels lying across to the bone-contacting surface end in a non-articulating area of the implant.

However, if the channels extend towards an articulating surface, it is preferred if the channels do not end on the articulating surface but preferably in the middle of the implant so that the mechanical stability of the implant is not influenced.

Channels with the aforementioned diameter or the aforementioned cross-sectional area extend from the surface of the implant, which is attached at the bone, in the inside of the implant. The channels of the preferably one-piece implants with opposite bone-contacting surfaces such as the cages, extend preferably through the implant to the opposite bone-contacting surface.

The channels of the implants preferably do not end at the height of the outer sheath, but reach to a maximum of 10 mm beyond its height.

The design of the channels follows a symmetry. It should be noted that a randomly originated channel network, such as exists for example in porous structures or sponges without symmetry are not satisfactory. The same is true for channels, which erratically change their directions and diameters and/or their random sequences and/or shapes resulting from multi-layer systems by chance. In such systems the blood flow is only increased in some areas and bone cell formation can only be seen in certain areas or punctual, a growth through the entire implant with bone cells is slowed or takes only place in part.

According to an embodiment, the channels run substantially parallel to each other and are straight, i.e. the channels have no turnings, bends, curves or the like, but run from their opening on an outer surface of the implant substantially parallel into the implant or a portion of the implant and end in the inside of the implant, or preferably run through the implant up to the opposite outer surface of the implant. Moreover, the channels preferably do not change their radius or diameter, neither continuously, nor rapid or stepwise, regardless of whether they are round, oval or polygonal channels.

The term "substantially parallel" is to be understood that there are certain manufacturing tolerances, and apart from these tolerances, the channels run parallel to each other.

It is also not mandatory that all channels are parallel to each other. There is also the possibility that an implant for example, has two anchor pins that are inserted into the bone and the two anchoring pins are not parallel to each other. Both anchoring pins can be provided with the channel structure, wherein the channels in one anchoring pin run substantially parallel to each other and this also applies to the channels of the other anchoring pin, the channels of the first anchoring pin, however, are not parallel to the channels of the second anchoring pin.

Thus, herein is referred to groups of channels, whereby the channels of a group are substantially parallel to each other but it is not mandatory that the groups of channels are parallel with each other.

Furthermore, the diameter of the channels do not change during their course, i.e. also, apart from manufacturing tolerances, the channels have substantially the same diameter from their beginning to their end.

It is also not mandatory that all channels start on the bone-contacting surface, i.e. to be in direct contact with the bone. Up to 30% preferably up to 20% of all channels can also begin in one area of the implant that is not directly in contact with the bone, i.e. preferably these channels start from the side of the bone-contacting surface.

On the other hand it is not necessary that the channels also end at a bone-contacting surface, which would only be the case anyway with one-piece bone-joining or bone-bridging implants. Up to 100% of all channels can also end at a surface not contacting the bone, but it is also possible that up to 100% of the channels end on the opposite bone-contacting surface, which is preferred for manufacturing reasons for one-piece cages according to an embodiment.

Moreover, it is preferred that, apart from the solid outer sheath of the implant, per $cm^2$ bone-contacting surface at least 50 channels start, preferably at least 100 channels and more preferably at least 150 channels. The channel structure comprises 20-1,000 channels per $cm^2$, preferably 50-750, more preferably 100-500, still more preferably 125-350 and especially preferably between 150 and 250 channels per $cm^2$.

Furthermore, the channels are interconnected. The channels are connected through openings with each other, wherein each channel has at least one opening to an adjacent channel. It is also preferred that the outer channels, i.e. those channels which form the outer row of the entire channel-type structure and abut to the solid outer sheath, have at least one opening to an adjacent channel and the channels which lie inside the channel-type structure have at least one opening to two adjacent channels, i.e. comprise absolutely at least two openings.

Moreover, it is preferred if the openings are arranged in a way that all channels are connected with each other, i.e. theoretically through one opening of one channel the entire channel-type structure could be filled with liquid such as blood. So preferably a three-dimensional interconnectivity of the entire structure is created.

The openings or so called connecting channels, can be designed as desired in the form of holes or cuts, and may be round, circular, point-like, cylindrical, oval, square, wedge-shaped or have any other configuration.

It is also preferred that the openings between the channels follow a pattern, i.e. a symmetry or a recurring order. It is therefore preferred that the openings between the channels run either along the longitudinal axis of the channels and the openings can have a maximum length, which corresponds to the length of the interconnecting channels. This type of openings, which run along the longitudinal axis of the channels, are preferably cuts, preferably wedge-shaped cuts in the channel walls or channel claddings.

It is also preferred that the openings between the channels follow a pattern, i.e. a symmetry or a recurring order. It is therefore preferred that the openings between the channels run either along the long axis of the channels and the openings can have a maximum length, which corresponds to the length of the interconnecting channels. This type of openings, which run along the long axis of the channels, are preferably cuts, preferably wedge-shaped cuts in the channel walls or channel wands.

Another type of openings is preferably designed round or oval and runs vertical to the longitudinal axis of the channels. The longitudinal axis of the channels runs along the long axis of the spine. These openings are cut into the implant with e.g. a laser and run through the outer wall of the implant in the direction of the opposite surface, thereby linking the channels on this line with each other. To ensure the above-described stability, the openings or connecting channels may also end in the inside of the cages without penetrating the opposite outer sheath. It is therefore preferred that these connecting channels pass through the outer sheath and end in front of the inner surface of the opposite outer sheath. However, preferred are openings or incisions, which run along the central axis of the channels and cut the wall of a channel along its entire length with a cut or tapered cut. These longitudinal cuts along the channel wall are naturally arranged in a way that several cuts in adjacent channel walls do not cut out parts of channel walls of the whole structure. Taking a look at FIG. 2 with the hexagonal channels and the wedge-shaped connecting channels or incisions, one could divide the channel walls in lateral wall areas and anterior-posterior wall areas. In FIG. 2, for example, only the lateral wall regions are cut in, so that all channel walls are at least connected in two places with the solid outer sheath and none of the wall segments, not even a segment of several channel wall areas of several channels of the total channel structure has been cut out or can be detached.

The diameter or the thickness of the openings is in the range of 0.1 µm to 1,000 µm, preferably in the range of 2 µm to 600 µm, more preferably 15 µm to 300 µm, even more preferably in the range of 25 µm to 120 µm and most preferably in the range of 40-90 µm.

Furthermore, the openings can extend along the longitudinal axis of the channels, this is referred to as continuous and can even run from one bone-contacting surface to the opposite bone-contacting surface and thus have the length of the channels themselves.

The openings may also occur in the form of drill-holes vertical to the longitudinal axis of the channels through the implant or as after certain intervals recurring openings in the channel walls connecting the channels with each other.

The design of the channels themselves is not essential, but their presence. It is obvious to a skilled person, that too many openings can affect the stability of the implant, so that a skilled person knows how to determine the number, size and location of the openings depending on the type of the implant.

Furthermore, the diameter or the thickness of the openings should be smaller than the diameter or the thickness of the channels and preferably less than one-tenth of the thickness of the channels.

For channels that are not continuous and end inside of the implant, such as channels, which would end on an articulating surface it is further advantageous if a channel connecting opening lies in the area where the channel ends in the implant.

Principally, the holes can be described as vertically to the longitudinal axis of the channels extending connecting channels. The channel structure consists preferably of substantially parallel channels, which also preferably extend parallel to the connecting channels.

It also goes without saying that not the whole implant must display the channel structure, but only the areas of an implant, which come into contact with the bone or particularly are embedded in the bone. However, it is still preferred if the inner channel structure of the intervertebral implants or cages extends from the underside of the overlying vertebral body to the upside of the underlying vertebral body. The interior of the implant is defined by the outer sheath.

Figure 5:
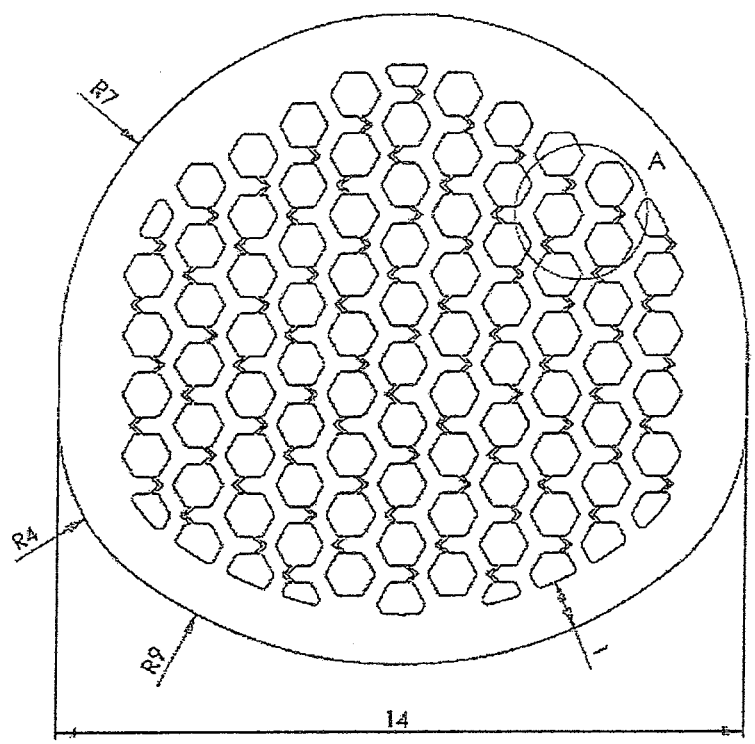
FIG. 5 once again shows the honeycomb structure as in FIG. 3 and marks a section that is shown enlarged in FIG. 6.
Figure 6:
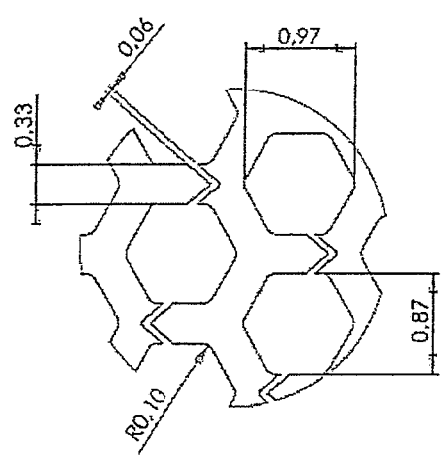
FIG. 6 shows the marked section of FIG. 5. The hexagonal structure of the channels and the wedge-shaped openings between the channels and the walls of the channels are shown enlarged.
Figure 7:
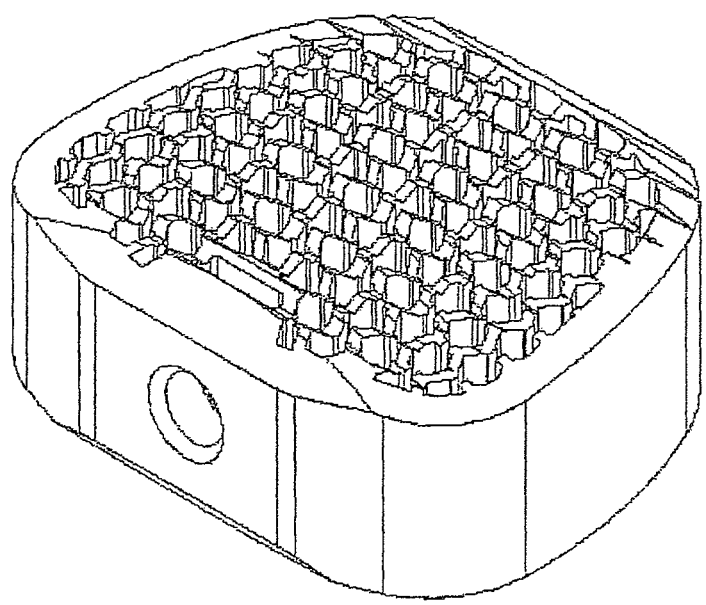
FIG. 7 shows an embodiment of the cage with a convex and serrated top and a convex and serrated bottom (not visible) or a convex raised inner honeycomb structure.
Figure 8:
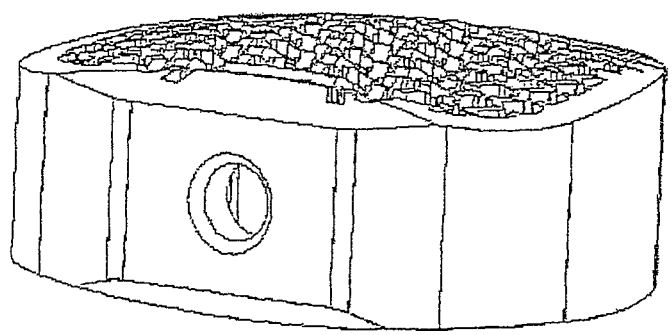
FIG. 8 shows another view of the cage according to FIG. 7, whereby the convex-designed top side and the convex-designed bottom are clearly visible.
Figure 9:
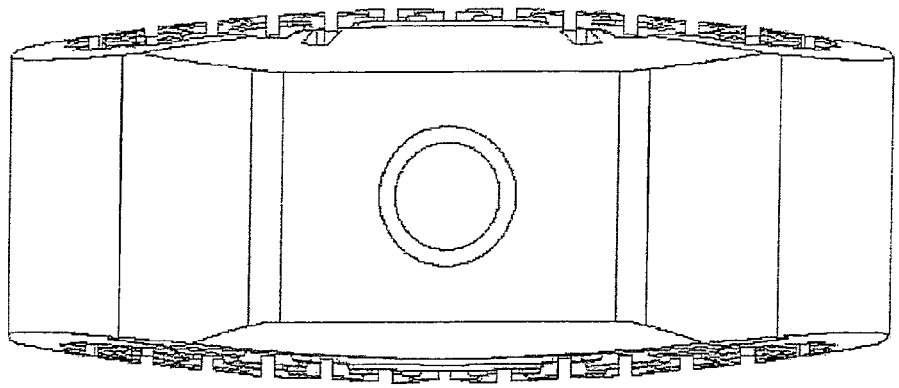
FIG. 9 shows a front view of the cage according to FIG. 7 with clearly visible convex top and bottom. The centrally shown round recess serves to hold an implantation tool.

In the embodiments of cages in particular have substantially parallel continuous channels proved to be advantageous, which by wedge-shaped longitudinal cuts along the longitudinal axis of the channels are connected, as shown in FIGS. 3, 5 and 6.

Furthermore, implants are preferred where the honeycomb structure, i.e. the inner channel structure, rises slightly over the substantially flat bone-contacting surface. Especially if the honeycomb structure of the implant protrudes over a solid border, the advantage of a high surface friction and therefore a very good anchorage is given and at the same time due to the low thickness of the honeycomb walls the possibility of mechanical movement of the same arises, which promotes the growth stimulation of the bone.

The walls between the individual channels, i.e. the honey-comb walls or channel walls have a thickness of 1 µm to 3,000 µm, preferably 5 µm to 1,000 µm, more preferably 10 µm to 500 µm and particularly preferably from 50 µm to 250 µm.

Moreover, it is preferred that the openings in the inner channel structure are arranged in such a way that the entire structure permits micro-movements preferably friction-movements. Such movement is possible e.g. with a structure as shown in FIG. 2, wherein the individual channels are connected by wedge-shaped longitudinal cuts in the lateral wall areas along the longitudinal axis of the channels. Thus, the individual channel walls can be shifted against each other according to the thickness of the wedge-shaped openings, so that micro-movements are possible.

Micro-movements are possible due to the channel-type or honeycomb structure. In order to stimulate bone growth and therefore to ensure a fast and stable growth of bone through the implant or the portion of the implant introduced in the bone, in addition to the channels provided in the implant, the cuts or notches are also provided in the channel walls. The channels promote blood flow and provide a large surface area for the attachment of new bone cells, whereby the notches or holes or cuts in the channel walls form a three-dimensional network, which connects all channels to each other, and also ensure that the channel walls are able to permit micro-movements. It is important that the notches or cuts are such that the channel walls can only move in a narrow range, which is defined by the thickness of the cut or the notches. Using the example of the above-discussed wedge-shaped cutouts a movement of the channel walls is only possible to the extent, such as the wedge tip can move in the cutout. From FIG. 6 it is very easy to see that the wedge-shaped cut allows a micro-movement in both lateral and in anterior-posterior direction. In the wedge-shaped cut, the wedge-shaped side of the channel wall can move inside and out of the wedge-shaped cut e.g. in lateral direction, limited by the thickness of the cut as well as the thickness of the cut across the wedge, and secondly, the wedge-shaped side of the channel wall can move e.g. in anterior and in posterior direction until it hits the V-shaped walls of the channel wall.

Figure 20:
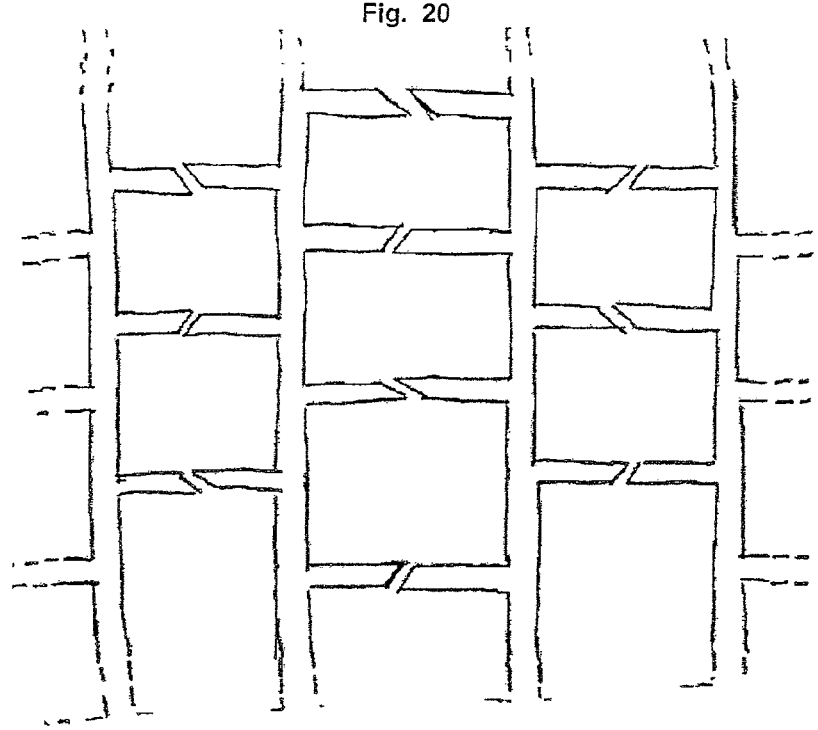
FIG. 20 shows a section of a channel-type structure of an implant with oblique cuts
Figure 21:
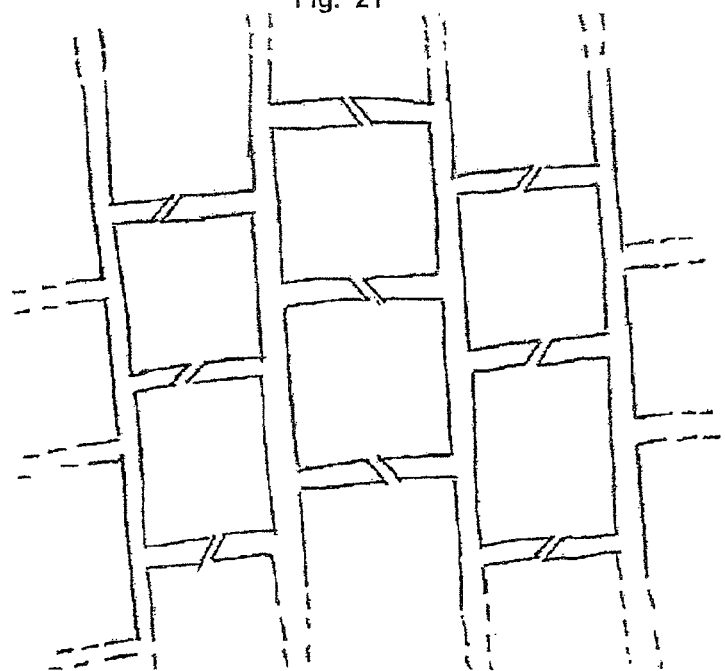
FIG. 21 shows a section of a channel-type structure of an implant with a further alternative for the disposal of oblique cuts or recesses While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

Thus, these V-shaped or wedge-shaped incisions are one possible embodiment to allow micro-movements of the entire channel-type structure. Another realization for the facilitation of micro-movements are the in FIG. 20 and FIG. 21 illustrated embodiments. FIG. 20 is a section of a channel-type structure of an implant as described in detail above. FIG. 21 is another possibility of arrangement of incisions to allow micro-movements. Of course, other possibilities are conceivable, which are within the skill of the average skilled person, as long as he knows what is to be intended with these openings, he will be able to design several other equivalent designs without inventive effort.

In these embodiments it is not necessarily the case that the cuts correspond to the length of the channels. The cuts along the longitudinal direction of the channels can have a length which corresponds to the channel length down to a length of 1 μm and preferably 5 μm and especially preferably 10 μm.

The thickness of the notch and the thickness of the cut is in the range of 0.1 μm to 1,000 μm, preferably in the range of 1 μm to 500 μm, more preferably 10 μm to 200 μm, even more preferably in the range of 30 μm to 100 μm and particularly preferably in the range of 50-80 μm. The thickness is referred to be the shortest distance between the incised channel wall from one side of the incision to the other. The thickness is given in FIG. 6 as 0.06 and corresponds to the distance by which the channel wall has been cut.

The length of the cuts corresponds to the length along the longitudinal axis of the channel. The depth of the incision is referred to as the path from the front-side of the channel wall to the back-side. In a straight incision, the depth of the cut is therefore the channel wall thickness.

In oblique or wedge-shaped incisions the depth of the cut corresponds to the 1.02-fold to 5-fold, preferably the 1.1-fold to 4.0-fold, more preferably the 1.3-fold to 3.0-fold, even more preferably the 1.4-fold to 2.5-fold and most preferably the 1.5-fold to 2.0-fold the channel wall thickness, i.e. the thickness of the channel wall from its front-side to the back-side.

If this type of configuration with the openings between the channels is combined with the configuration, where the inner channel-type structure rises like an island up to several millimeters over the basically flat bone-contacting area, i.e. is designed convex in the direction of the contacted vertebral body, this up to 10 mm raised portion of the honeycomb structure stimulates the growth of bone particularly well, because this elevated part digs slightly into the bone and through its property to permit micro-movements, it can follow the bone movements and also promotes the growth of bones through a slight but continuous stimulation.

Implants with bone growth stimulating surfaces are still a subject of research, without having achieved a satisfactory result yet. The previously described raised honeycomb structure with the ability to permit micro-movements, in particular microfriction-movements seems to be the long sought solution to stimulate bone growth in an optimal way and to lead to a rapid growth of bone through the entire implant.

This channel structure for bone-contacting, bone joining or bone-bridging implants has surprisingly shown to be very advantageous in terms of an ingrowth of bone tissue and providing a solid merging with the contacted bone.

Furthermore, the honeycomb structure combines the features of good mechanical stability and at the same time preserves optimal filling volume, so that a rapid and stable growth of bones through the implant can take place.

Bone tissue generally comprises three cell types, osteoblasts, osteocytes and osteoclasts, whereby the developed bone also has a bone top layer of bone lining cells. The presence of blood is needed for optimal bone formation. In the formation of bones the osteoblasts, osteocytes and osteoclasts work together. Osteoblasts are bone producing cells and responsible for building and maintaining the bone. None active osteoblasts on the bone surface are called bone lining cells. Osteocytes are former osteoblasts that are incorporated in the bone tissue by ossification. They provide for the preservation of the bone by adjusting the bone resorption to the bone formation. Osteoclasts are responsible for the degradation of the bone. Through them, the thickness of the bone is determined and calcium and phosphate are released from the bone. The osteoblasts are the cells responsible for bone formation. They develop from undifferentiated mesenchymal cells, embryonic connective tissue cells. They attach themselves to bones like dermal layers and indirectly form the basis for new bone substance, the bone matrix, especially by excreting calcium phosphate and —carbonate in the interstitial space. In this process they change to a scaffold of osteocytes no longer capable of dividing, which is slowly mineralized and filled with calcium.

The channel structure seems to promote the inflow of blood and thus osteoblasts, which fill the channel space quickly and lead to a significantly better growth of the bone together with the implant compared to what conventional implants are capable of.

Furthermore, the designed implants have the advantage compared to, for example, porous structures and sponges that they are not very deformable and are dimensionally stable, possess a defined shape and surface and can be handled by conventional implantation tools and can be implanted without running the risk to damage or destroy the implant or the channel-like structure in the implant.

In order to promote the adhesion of bone cells even more, the inner surfaces of the channels can be structured, for example, any mechanical, chemical or physical roughening. To suppress the growth of bacteria or other germs on the implant surface, it can be provided with antibiotics and the outer surface of the outer sheath for example can be provided with a drug eluting coating, in which agents such as antibiotics are stored and can be released continuously.

EXAMPLES

Preferred embodiments of the device will now be discussed on the basis of the examples, bearing in mind that the examples discussed reflect advantageous embodiments of the invention, but do not limit the scope of protection to these embodiments.

Example 1

Cage

Example 1 relates to a cage, especially a cervical cage with a longitudinal diameter of 14 mm and a transverse diameter of 12 mm and a height of 8 mm. The Cage is nearly oval and the longitudinal diameter is understood to be the maximum diameter and the transverse diameter is understood to be the smallest diameter.

The cage is made of titanium with a solid at least 1.1 mm thick outer sheath and an upper and lower flat surface for contact with the respective vertebral bodies.

Inside the cage a honeycomb structure of channels is formed with hexagonal walls. The channels extend in a straight line from the top of the bone-contacting surface to the opposite lower vertebral contacting flat surface. Per $cm^2$ bone-contacting surface about 34-42 channels are available.

The channels have a diameter of 870-970 μm specified as the distance between two opposing parallel walls.

The channels are also connected with each other through notches in the channel walls. The notches have a wedge-shaped structure, as shown in FIG. 2, so that the channel walls can be shifted laterally only by the thickness of the notches against each other, which contributes to an increased stability of the implant. The notch has a thickness of 60 μm.

Example 2

Cage

Example 2 relates to a cage, especially one with a cervical cage of longitudinal diameter 16 mm and a transverse diameter of 13 mm and a height of 9 mm. The cage is nearly oval and the longitudinal diameter is understood to be the maximum diameter and the transverse diameter is understood to be the smallest diameter.

The cage consists of zirconium with a massive 1.2 mm-thick outer sheath and an upper and lower surface for contact with the respective vertebral bodies. The upper edge of the outer sheath is flat and serves to support the upper vertebral body. The inner channel structure rises from the edge of the outer sheath in a convex shape up to 4 mm beyond the edge of the outer sheath, so that the channel structure in the middle of the cage can press up to 4 mm into the underside of the overlying vertebral body. On the opposite side of the cage the inner honeycomb or canal-type structure also extends like a spherical surface in a convex shape toward the upper surface of the underlying vertebral body and digs up to 4 mm in the central region and accordingly less in the edge areas of the lower vertebral body.

Inside the cage a honeycomb structure of round channels is formed. The channels extend in a straight line from the top of the upper vertebral body contacting surface to the opposite the other lower vertebral contacting surface. Per $cm^2$ bone-contacting surface about 40 channels are available.

The channels have a diameter of 850 μm and the thickness of the channel walls is 350 μm.

The channels are also connected through notches in the channel walls with each other, which are arranged in the form of longitudinal incisions. These longitudinal incisions cut the channel wall along its entire length. The longitudinal incisions however, do not cut the channel wall in the shortest way possible, which is 350 μm, but cut the channel wall at an angle on a distance of about 370 μm in e.g. east-west direction. The opposite side of the channel is cut with a longitudinal incision through a distance of about 370 microns, but now in west-east direction. The thickness of the longitudinal cut, i.e. of the connecting channel is 50 μm.

Such a honeycomb structure allows for micro-movements and digs up to 4 mm into the overlying and underlying vertebral body, whereby the growth of bones is strongly stimulated, so that a fast and good growth of newly formed bone through the implant occurs.

Example 3

Cage

Example 3 relates to a cage, especially a thoracic cage with a longitudinal diameter of 10 mm and a transverse diameter of 8.8 mm and a height of 6.5 mm. The Cage is nearly oval and the longitudinal diameter is understood to be the maximum diameter and the transverse diameter is understood to be the smallest diameter.

Figure 10:
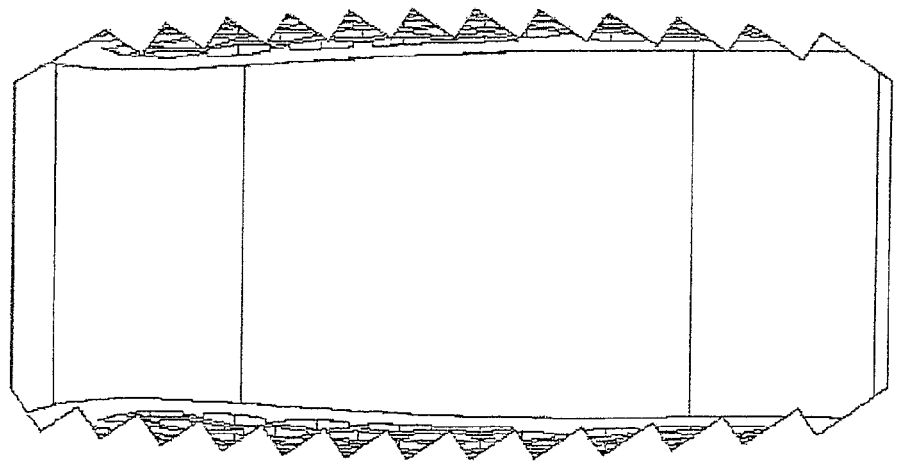
FIG. 10 shows a side view of an intervertebral implant with a serrated top and serrated bottom. The teething is located in the honeycomb structure and in the outer sheath and serves to stabilize the position of the implant between the vertebral bodies after implantation.
Figure 11:
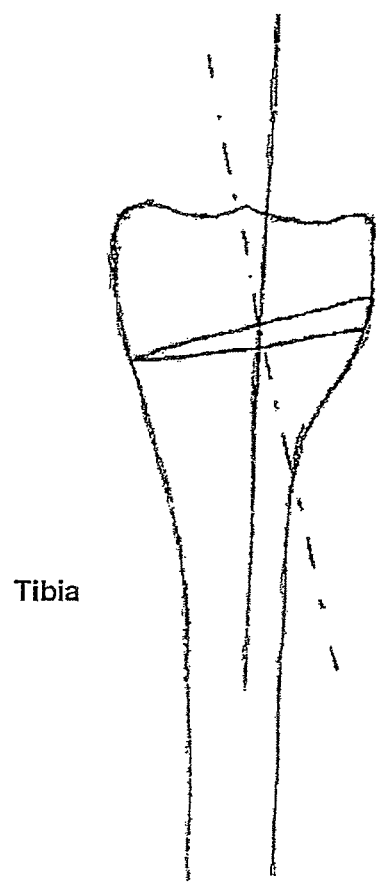
FIG. 11 shows a lower leg bone (tibia) with an implanted angle implant.
Figure 12:
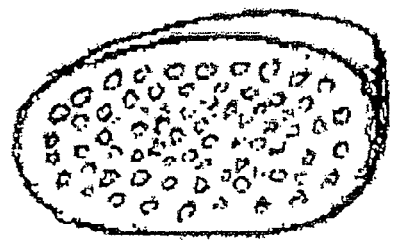
FIG. 12 shows the inserted angle implant according to FIG. 5.
Figure 13:
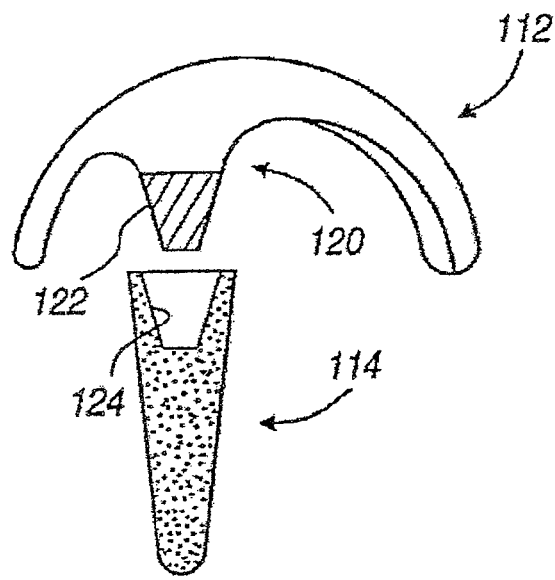
FIG. 13 shows an anchoring pin (114) for a ball joint implant (112). The anchoring pin is fully inserted into the bone and has the honeycomb structure, which is represented by dots. The individual channels run along the longitudinal axis of the anchoring pin and are connected through openings, which lead in part through the outer walls, so that the openings of the channels are not only at the tip of the pen but also on the sides.
Figure 14:
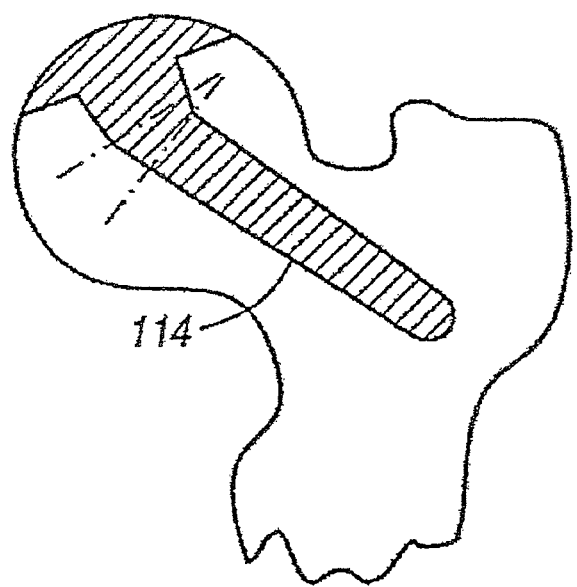
FIG. 14 shows the full implant according to FIG. 7 after implantation.

The Cage consists of PEEK, which gets employed in medical technology, with a solid at least 0.9 mm thick outer sheath and an upper and lower flat surface for contact with the respective vertebral bodies, wherein the top and the bottom of the cage has been jagged or serrated with a height of the teeth of about 0.5 mm. Such shaped upper and lower surfaces are shown for example in FIG. 4 and FIG. 10.

Inside of the cage a channel-type structure is formed from channels with square walls. The channels extend in a straight line from the top of the upper vertebral body contacting surface to the opposite the other lower vertebral contacting surface. Per $cm^2$ bone-contacting surface about 30-33 channels are available.

The channels have a diameter of about 800 μm, specified as the distance between two opposing parallel walls.

The channels are also connected with each other through notches or incisions in the channel walls. The notches or incisions have a linear structure and cut the channel walls on the shortest way possible, whereby only channel walls running parallel to each other are cut so that no channel wall components are cut out from the channel-type structure. The notches or incisions have a thickness of 30 μm.

Example 4

Cage

The Cage according to Example 4 is made of titanium and has the same dimensions as the Cage in Example 1 but additionally also has a toothed top and toothed bottom with a maximum height of the teeth of 0.75 mm.

Furthermore, the notches in the channel walls are not wedge-shaped and do not extend over the entire length of the canal wall. The notches, however, are designed as oval oblong holes in the channel walls with a transverse diameter of 7 μm and a longitudinal diameter of 20 μm.

Example 4

Artificial Intervertebral Disc

An embodiment of an intervertebral disc implant consists of a cover plate, a vertebral intermediate plate and a base plate.

The intervertebral disc implant has a size that is suitable for replacing a L3/4 vertebral segment. Smaller embodiments of the described intervertebral disc implant can be produced by someone skilled in the art without any problems. The vertebral intermediate plate consists of UHMWPE.

The cover plate is made of titanium used in medical technology. The surface of the base plate facing the bone has the channel-type structure of channels which extend through the cover plate.

The channels are round shaped and have a diameter of 400-600 μm.

Per cm² surface of the bone-contacting surface of the cover plate approximately 88-200 channels are available.

In the area, where the cover plate comes in contact with (contact area) or can come in contact with (articulating surface) the vertebral intermediate plate, preferably fewer channels or no continuous channels or no channels are arranged, compared to the non-articulating area of the vertebral intermediate plate.

The base plate is also made of titanium. The surface of the base plate facing the bone may be solid or have the channel structure.

In a preferred embodiment the base plate shall exhibit a similar channel structure like the cover plate, whereby it is again preferred that the vertebral intermediate plate and articulating surface have fewer or no continuous or no channels at all.

However, it is also possible to provide only the base plate with the channel-type structure and not the cover plate.

Example 5

Artificial Intervertebral Disc

An embodiment of an intervertebral disc implant consists of a cover plate with integrated intervertebral intermediate plate and a base plate.

The cover plate is designed spherical on the side facing the base plate and thus includes the intervertebral intermediate plate as tightly integrated component. The base plate has a corresponding spherical recess for receiving the cover plate. Base plate and cover plate are made of titanium, whereby the articulating surface is hardened by a ceramic coating of Ti—Nb—N.

The channel structure extends through the cover plate with the integrated intervertebral intermediate plate from the bone-contacting surface up to the surface facing the base plate. In the area of the articulating surface, i.e. a hard-hard-pairing, where the base plate may come into contact with the cover plate, the channels are not continuous, but end around the middle of each plate. These non-continuous channels are at the closed end which is approximately at the middle of each plate and are connected by lateral openings to the adjacent channels, so that when liquids enters, particularly blood and tissue fluid, the air can escape from these channels through the side openings.

The base plate can also have the channel structure, whereby the channels are preferably arranged only in the non-articulating surface.

The channels are round shaped and have a diameter of 200 μm.

Per cm² bone-contacting surface of the cover plate about 700-800 channels are available.

Example 6

Anchoring Pins from Tibial or Femoral Components

Anchoring pins from a femoral or tibial component or the shaft of a hip stem, or a femoral neck prosthesis are provided along their longitudinal direction or along their transverse direction with the honeycomb structure or channel structure.

The channels can be round or square and are provided with notches in such a way, that the micro-movements are possible. Channel number and diameter as well as the thickness of the notches are in the size range as described in Example 1, 2 or 3.

Figures 15, 16:
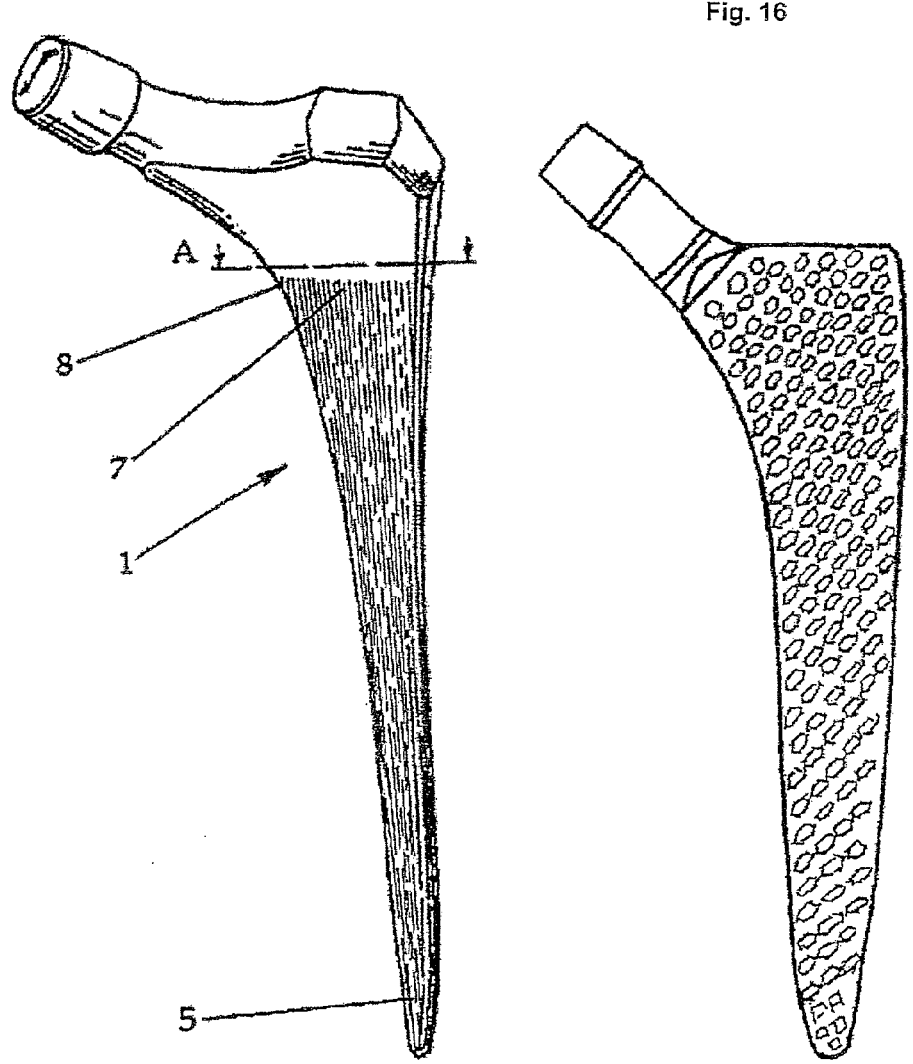
FIG. 15 shows a hip stem (1), exhibiting the honeycomb structure in the shaft area (from No. 8 to No. 5). The channels (7) extend from the top of the hip joint implant but do not end at the opposite lying surface but approximately at the height of the line A and are connected through openings. The channels (7) run parallel to the surface A to the tip (5) of the hip joint implant (1).
FIG. 16 shows a hip stem with a vertical to the longitudinal axis of the shaft extending channel structure. A course of the channels along the longitudinal axis of an implant is not mandatory as illustrated by FIG. 9B. The openings between the individual channels are not shown but present, which results in a clear three-dimensional network of canals.
Figure 17:
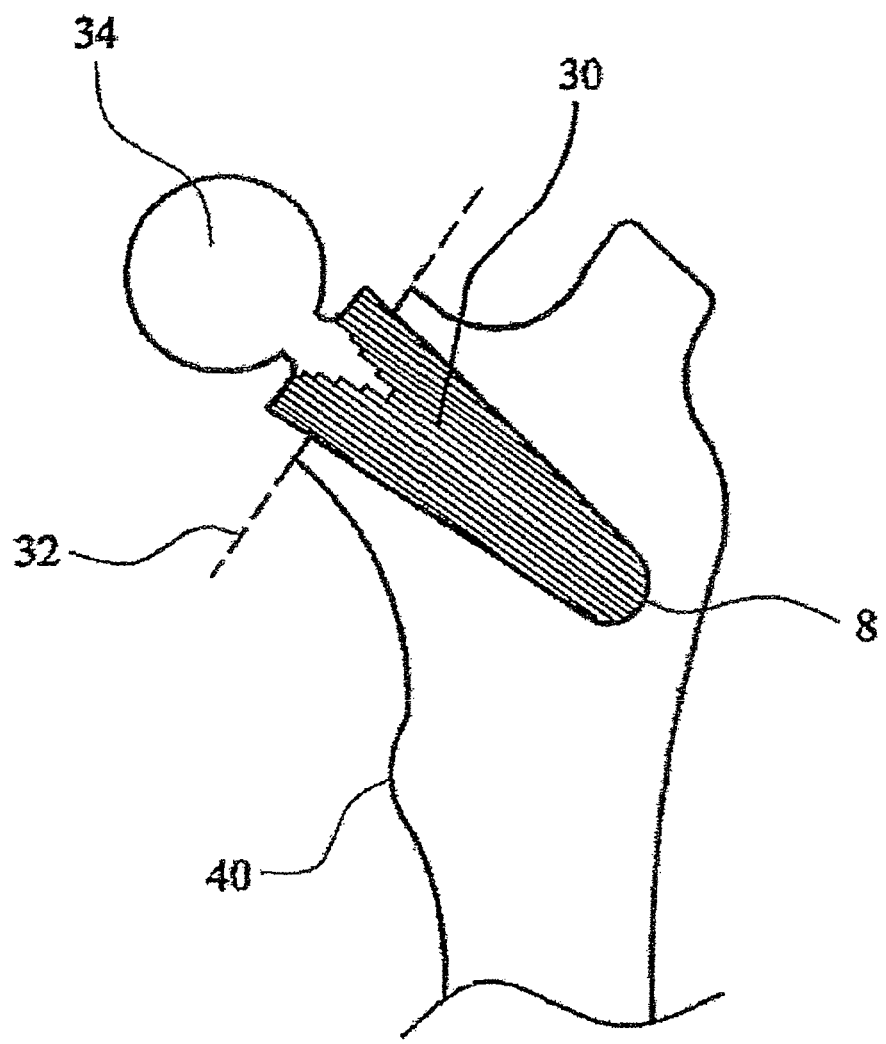
FIG. 17 shows a femoral neck prosthesis with a ball head (34) and an anchoring pin (8). The anchoring pin is implanted up to the surface (32) into the bone and exhibits the channel structure (30). The channels extend substantially parallel from the tip of the anchoring pin (8) to the opposite surface. The channels end prematurely in the area of the ball head (34) and do not nm into the ball head. The channels are connected through lateral openings (not shown) preferably vertical to the course of the channels, which results in a clear three-dimensional network of canals.
Figure 18:
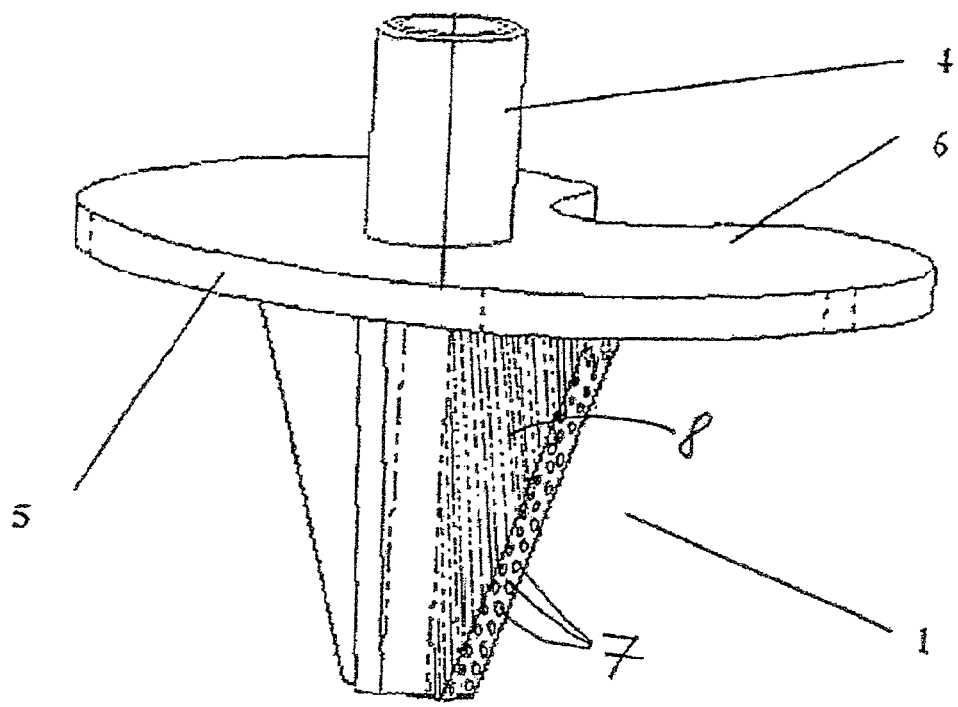
FIG. 18 shows a tibial component (a) of a knee joint implant with a surface (6) and a pin (4) to receive the tibial onlays (not shown). The tibial component (a) has a wedge-shaped anchoring pin with the channel structure (8). The individual channels (7) extend substantially in parallel from the top and the sides of the anchoring pin to the lower edge (5) of the contact surface of the tibial onlays (6), but do not extend through the contact surface (6). The channels are also connected to each other through lateral openings (not shown), thus resulting in a three-dimensional channel network.
Figure 19:
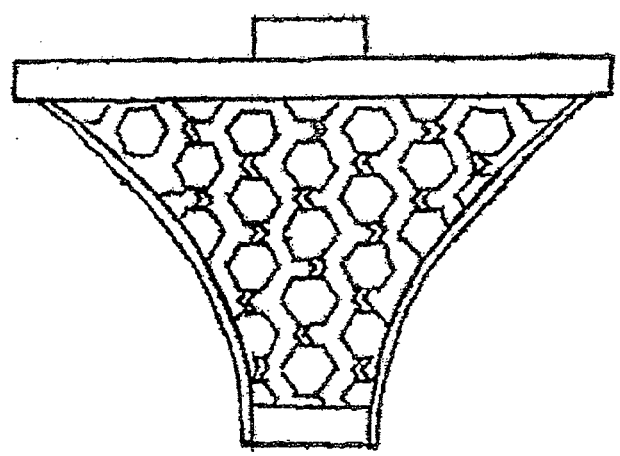
FIG. 19 shows a tibial component of a knee joint implant with the channel structure (not true-to-scale). The channels are clearly oversized for a better display, so that the structure of the channels to each other and the wedge-shaped openings between the channels can be seen better.

In contrast to the cages described in Example 1, 2 or 3, the channels end in the implant, when they progress in the longitudinal direction of the implant, as shown for example in the shaft of the implant according to FIG. 15, they end only partly in the implant, as with the pin of the femoral neck prosthesis according to FIG. 17 or can extend through the implant, when the channels extend in the transverse direction of the implant, as shown in the shaft of the implant according to FIG. 16.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

The invention claimed is:

1. Intervertebral implant, wherein the implant comprises: two surfaces for contacting two vertebral bodies, an inner structure; and an outer sheath which surrounds the inner structure; wherein the inner structure comprises a channel structure that is formed by a plurality of vertical channels running along a longitudinal axis of spinal column and a plurality of horizontal channels running horizontally from one side to opposite side of the implant, wherein each vertical channel is connected by a horizontal channel with at least two openings with adjacent vertical channels, the openings extending continuously from one bone-contacting surface to the opposite surface in form of cuts; wherein the openings are located either only in lateral areas or only in anterior-posterior areas of channel walls.

2. Intervertebral implant according to claim 1, wherein the vertical channels have a cross-sectional area of 8,000 μm² to 70,000 μm².

3. Intervertebral implant according to claim 1, wherein the vertical channels and the horizontal channels have a diameter of 100 μm to 3,000 μm.

4. wherein the outer sheath surrounds the inner structure partly at two opposite sides.

5. Intervertebral implant according to claim 1, wherein the bone-contacting surface of the inner structure is convex.

6. Intervertebral implant according to claim 1, wherein the vertical channels extend continuously from one bone-contacting surface to the opposite surface.

7. Intervertebral implant according to claim 1, wherein the implant has at least 100 vertical channels per cm² of bone-contacting surface.

8. Intervertebral implant according to claim 1, wherein the vertical and horizontal channels are shaped round, oval, triangular, square, pentagonal or hexagonal.

9. Intervertebral implant according to claim 1, wherein the vertical channels do not change their radius or diameter during the course.

10. The intervertebral implant according to claim 9, wherein the outer sheath surrounds the inner structure partly at two opposite sides.

11. The intervertebral implant according to claim 9, wherein the bone-contacting surface of the inner structure is convex.

12. The intervertebral implant according to claim 9, wherein the vertical channels extend continuously from one bone-contacting surface to the opposite surface.

13. The intervertebral implant according to claim 9, wherein the implant has at least 100 vertical channels per cm2 of bone-contacting surface.

14. The intervertebral implant according to claim 9, wherein the channels are shaped round, oval, triangular, square, pentagonal or hexagonal.

15. The intervertebral implant according to claim 9, wherein the vertical channels do not change their radius or diameter during the course.

16. The intervertebral implant according to claim 9, wherein the horizontal channels run straight through the implant so that an X-ray beam can go through or pass through the implant.

17. The intervertebral implant according to claim 9, wherein the implant is selected from the group including cervical cages, thoracic cages, lumbar cages, artificial intervertebral discs and implants for the fusion of vertebrae.

18. The intervertebral implant according to claim 9, wherein the horizontal channels do not change their radius or diameter during the course.

19. An intervertebral implant comprising: two surfaces for contacting two vertebral bodies, an inner structure, and an outer sheath which surrounds the inner structure, wherein the inner structure comprises a channel structure that is formed by a plurality of vertical channels running along the longitudinal axis of the spinal column and a plurality of horizontal channels running horizontally from one side to the opposite side of the implant, wherein openings between the vertical channels are point-shaped, punctiform, circular, cylindrical, oval or wedge-shaped and the openings extend continuously from one bone-contacting surface to the opposite surface in the form of cuts and wherein the openings are located either only in the lateral areas or only in the anterior-posterior areas of channel walls.

20. The intervertebral implant according to claim 19, wherein the vertical channels and the horizontal channels have a cross-sectional area of 8,000 $\mu m^2$ to 70,000 $\mu m^2$.

21. The intervertebral implant according to claim 19, wherein the vertical channels and the horizontal channels have a diameter of 100 $\mu m$ to 3,000 $\mu m$.

22. An intervertebral implant comprising: two surfaces for contacting two vertebral bodies, an inner structure, and an outer sheath which surrounds the inner structure, wherein the inner structure comprises a channel structure that is formed by a plurality of vertical channels running along a longitudinal axis of spinal column and a plurality of horizontal channels running horizontally from one side to opposite side of the implant, wherein the inner structure of the implant permits micro-movements due to wedge-shaped or oblique openings in form of longitudinal cuts along channel wall.

23. The intervertebral implant according to claim 22, wherein the vertical channels and the horizontal channels have a cross-sectional area of 8,000 $\mu m2$ to 70,000 $\mu m2$.

24. The intervertebral implant according to claim 22, wherein the vertical channels and the horizontal channels have a diameter of 100 $\mu m$ to 3,000 $\mu m$.

25. The intervertebral implant according to claim 22, wherein the outer sheath surrounds the inner structure partly at two opposite sides.

26. The intervertebral implant according to claim 22, wherein the bone-contacting surface of the inner structure is convex.

27. The intervertebral implant according to claim 22, wherein the vertical channels extend continuously from one bone-contacting surface to the opposite surface.

28. The intervertebral implant according to claim 22, wherein the implant has at least 100 vertical channels per cm2 of bone-contacting surface.

29. The intervertebral implant according to claim 22, wherein the channels are shaped round, oval, triangular, square, pentagonal or hexagonal.

30. The intervertebral implant according to claim 22, wherein the vertical channels do not change their radius or diameter during the course.

31. The intervertebral implant according to claim 22, wherein the horizontal channels run straight through the implant so that an X-ray beam can go through or pass through the implant.

32. The intervertebral implant according to claim 22, wherein the implant is selected from the group including cervical cages, thoracic cages, lumbar cages, artificial intervertebral discs and implants for the fusion of vertebrae.

33. The intervertebral implant according to claim 22, wherein the horizontal channels do not change their radius or diameter during the course.

* * * * *